United States Patent
Li et al.

(10) Patent No.: US 10,532,963 B2
(45) Date of Patent: Jan. 14, 2020

(54) METHODS FOR THE OXIDATIVE DEHYDROGENATION OF BUTENE TO PRODUCE BUTADIENE

(71) Applicants: SABIC Global Technologies B.V., Bergen op Zoom (NL); Xin Li, Sugar Land, TX (US); Jorge Jimenez, Sugar Land, TX (US); Paulette Hazin, Sugar Land, TX (US); Reggie Tennyson, Sugar Land, TX (US); Xiankuan Zhang, Sugar Land, TX (US)

(72) Inventors: Xin Li, Sugar Land, TX (US); Jorge Jimenez, Sugar Land, TX (US); Paulette Hazin, Sugar Land, TX (US); Reggie Tennyson, Sugar Land, TX (US); Xiankuan Zhang, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/062,541

(22) PCT Filed: Jan. 5, 2017

(86) PCT No.: PCT/IB2017/050036
§ 371 (c)(1),
(2) Date: Jun. 14, 2018

(87) PCT Pub. No.: WO2017/122103
PCT Pub. Date: Jul. 20, 2017

(65) Prior Publication Data
US 2018/0362419 A1 Dec. 20, 2018

Related U.S. Application Data

(60) Provisional application No. 62/277,353, filed on Jan. 11, 2016.

(51) Int. Cl.
C07C 5/48 (2006.01)
B01J 23/00 (2006.01)
(Continued)

(52) U.S. Cl.
CPC ............ C07C 5/48 (2013.01); B01J 23/002 (2013.01); B01J 27/10 (2013.01); C07C 11/167 (2013.01);
(Continued)

(58) Field of Classification Search
None
See application file for complete search history.

(56) References Cited

U.S. PATENT DOCUMENTS

| | | | |
|---|---|---|---|
| 3,607,966 A | 9/1971 | Croce et al. | 585/625 |
| 3,998,760 A | 12/1976 | Christmann et al. | 502/324 |

(Continued)

FOREIGN PATENT DOCUMENTS

| | | |
|---|---|---|
| CN | 103073382 A | 5/2013 |
| CN | 103304359 A | 9/2013 |

(Continued)

OTHER PUBLICATIONS

Welch et al. "Butadiene via oxidative dehydrogenation," Hydrocarbon Processing, 57 (11), Nov. 1978, pp. 131-136.
(Continued)

*Primary Examiner* — Ali Z Fadhel
(74) *Attorney, Agent, or Firm* — Norton Rose Fulbright US LLP

(57) ABSTRACT

Methods for producing butadiene by the oxidative dehydrogenation of butene are provided. Methods for producing butadiene from a feed stream including oxygen and butene in a molar ratio of oxygen to butene ($O_2/C_4H_8$) from about 0.9 to about 1.5 can include introducing the feed stream to a catalyst in the presence of steam. The molar ratio of steam (Continued)

to butene ($H_2O/C_4H_8$) can be from about 10 to about 20. Methods can further include reacting the butene to generate a product stream therefrom comprising butadiene and water. Methods can further include separating water from the product stream to generate a butadiene stream including greater than about 85 wt-% butadiene.

20 Claims, 3 Drawing Sheets

(51) Int. Cl.
    *B01J 27/10*     (2006.01)
    *C07C 11/167*     (2006.01)

(52) U.S. Cl.
    CPC ........ *B01J 2523/22* (2013.01); *B01J 2523/23* (2013.01); *B01J 2523/27* (2013.01); *B01J 2523/842* (2013.01); *B01J 2523/845* (2013.01); *C07C 2523/745* (2013.01); *C07C 2523/80* (2013.01)

(56) References Cited

U.S. PATENT DOCUMENTS

| | | | |
|---|---|---|---|
| 4,150,064 A | 4/1979 | Miklas | 585/625 |
| 4,332,972 A | 6/1982 | Christmann et al. | 585/442 |
| 8,513,479 B2 | 8/2013 | Chung et al. | 585/629 |
| 2004/0034266 A1* | 2/2004 | Brophy | B01J 19/0093 585/658 |
| 2013/0217568 A1* | 8/2013 | Hazin | B01J 27/138 502/226 |
| 2016/0318829 A1* | 11/2016 | Gaertner | C07C 5/2512 |

FOREIGN PATENT DOCUMENTS

| | | |
|---|---|---|
| CN | 104001533 A | 8/2014 |
| CN | 103102238 B | 12/2014 |
| CN | 103055871 B | 7/2015 |
| EP | 2873458 A1 | 5/2015 |
| WO | WO2014138510 A1 | 9/2014 |
| WO | WO2015090998 A1 | 6/2015 |

OTHER PUBLICATIONS

International Search Report and Written Opinion from PCT/IB2017/050036, dated Apr. 13, 2017, 11 pages.
Lee et al. "Oxidative Dehydrogenation of n-Butene to 1,3-Butadiene over Sulfated $ZnFe_2O_4$ Catalyst." Cat. Lett. (2009)133 (3/4) 321-327.

* cited by examiner

METHODS FOR THE OXIDATIVE DEHYDROGENATION OF BUTENE TO PRODUCE BUTADIENE

CROSS-REFERENCE TO RELATED APPLICATIONS

This application is a national phase application under 35 U.S.C. § 371 of International Application No. PCT/IB2017/050036 filed Jan. 5, 2017, which claims priority to U.S. Provisional Patent Application No. 62/277,353 filed Jan. 11, 2016. The entire contents of each of the above-referenced disclosures is specifically incorporated by reference herein without disclaimer.

FIELD

The disclosed subject matter relates to methods for the oxidative dehydrogenation of butene to produce butadiene.

BACKGROUND

Butadiene is a simple conjugated diene having the formula $C_4H_6$. Butadiene can be a raw material in the manufacture of many useful articles, including adhesives, sealants, coatings, hoses, and rubber articles such as automobile tires, and shoe soles. For example, butadiene can be used as a monomer in the production of synthetic rubber. Butadiene can also be used as a raw material for producing certain chemical intermediates such as adiponitrile and chloroprene, which can in turn be used to produce nylon and neoprene.

Butadiene can be found in the hydrocarbon streams produced by certain cracking processes, e.g., steam cracking of naphtha, gas cracking, and catalytic cracking of gas oil and/or vacuum gas oil. Certain methods of manufacturing butadiene are known in the art. For example, Chinese Patent Publication No. CN103304359 discloses a method for producing butadiene from a mixed $C_4$ hydrocarbon stream, which includes the oxidative dehydrogenation of butene in the hydrocarbon stream. Chinese Patent Publication No. discloses a process for the oxidative dehydrogenation of butene to butadiene using a ferrite catalyst. Chinese Patent Publication No. CN103055871 discloses a process for generating butadiene including the oxidative dehydrogenation of butene using a zinc-ferrite catalyst. European Patent Publication No. EP2873458 discloses iron oxide catalysts having another metal component for use in the oxidative dehydrogenation of butene to butadiene. U.S. Pat. No. 8,513,479 discloses certain methods of making and using zinc-ferrite catalysts for an oxidative dehydrogenation reaction.

However, there remains a need for improved techniques for the oxidative dehydrogenation of butene to produce butadiene.

SUMMARY OF THE DISCLOSED SUBJECT MATTER

The disclosed subject matter provides methods for the oxidative dehydrogenation of butene to produce butadiene.

In certain embodiments, an exemplary method for producing butadiene from a feed stream including oxygen and butene in a molar ratio of oxygen to butene ($O_2/C_4H_8$) from about 0.9 to about 1.5 can include introducing the feed stream to a catalyst in the presence of steam. The molar ratio of steam to butene ($H_2O/C_4H_8$) can be from about 10 to about 20. The method can further include reacting the butene to generate a product stream including butadiene and water. The method can further include separating at least a portion of the water from the product stream to generate a butadiene stream including greater than about 85 wt-% butadiene.

In certain embodiments, the molar ratio of oxygen to butene ($O_2/C_4H_8$) in the feed stream can be about 1. The feed stream can further include a diluent. The diluent can include methane, nitrogen, helium, argon, and/or combinations thereof. The molar ratio of steam to butene ($H_2O/C_4H_8$) can be from about 11 to about 13.

In certain embodiments, the catalyst can be a zinc-ferrite catalyst. The zinc-ferrite catalyst can have the formula $FeZn_aCo_bMg_cCa_dCl_eM_fO_x$. Subscripts a, b, c, d, e, f, and x can correspond to a molar ratio relative to 1 mol of Fe, and a can range from about 0.07 to about 0.7, b can range from about 0.01 to about 0.20, c can be less than or equal to about 0.40, d can be less than or equal to about 0.40, e can be less than or equal to about 0.10, and f can be less than or equal to about 0.20. M can be a metal from one or more of Co, Mg, Ca, Ag, Al, Ce, Cs, Cu, K, La, Li, Mn, Mo, Na, Ni, P, Pd, Pt, Ru, Si, V, W, and/or Y.

The zinc-ferrite catalyst can be prepared from a Zn precursor, a Fe precursor, a Co precursor, optionally a Mg precursor, optionally a Ca precursor, and optionally a M precursor. In certain embodiments, the Zn precursor contains initial Zn and the Fe precursor contains initial Fe, and the molar ratio of initial Zn to initial Fe is less than or equal to about 0.35.

In certain embodiments, the molar ratio of steam to butene ($H_2O/C_4H_8$) can be about 12. The steam can be mixed with the feed stream prior to introducing the feed stream to the catalyst. The reaction can be performed under isothermal and/or non-adiabatic conditions. In certain embodiments, the reaction can be performed at a temperature from about 330° C. to about 370° C.

In certain embodiments, the reaction is an oxidative dehydrogenation reaction. The reaction can have butadiene selectivity greater than about 92%. Butene conversion can be from about 90% to about 95%. Oxygen conversion can be from about 90% to about 99%.

DETAILED DESCRIPTION

The presently disclosed subject matter provides methods for producing butadiene from butene and oxygen.

Figure 1:
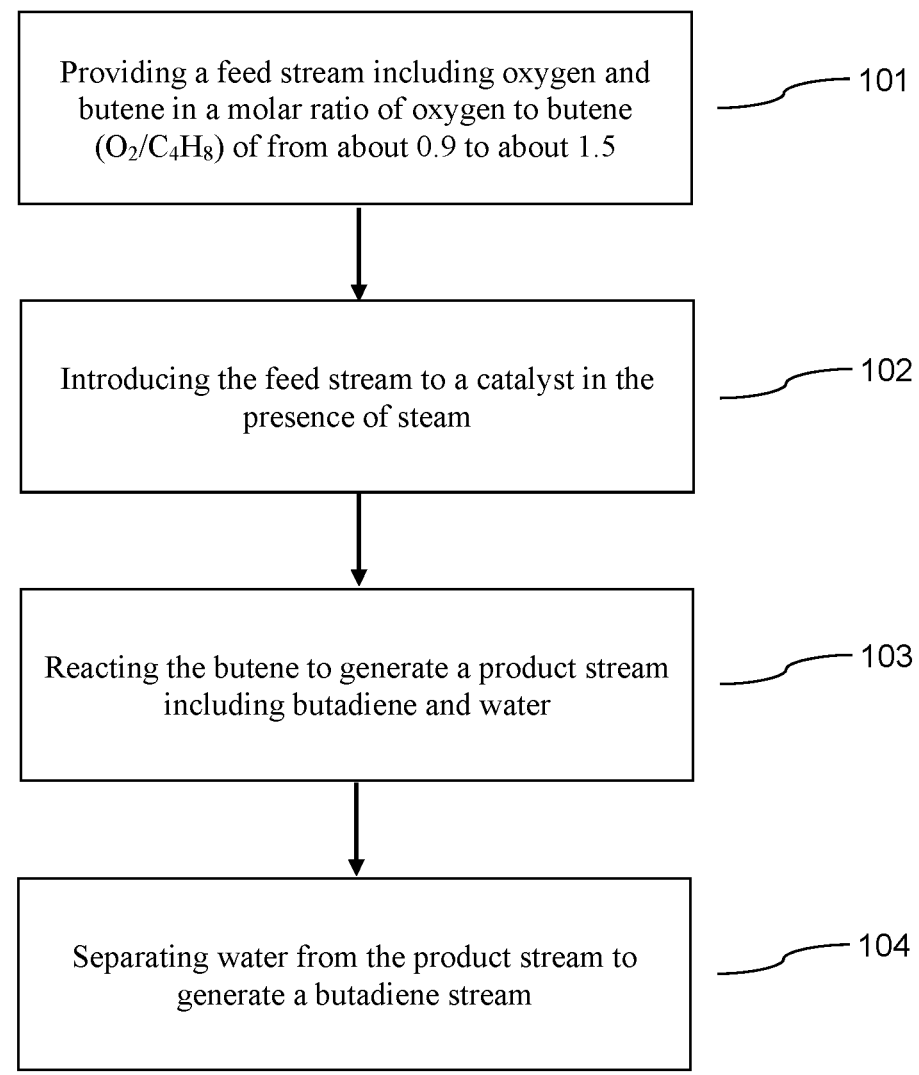
FIG. 1 depicts a method for the oxidative dehydrogenation of butene according to one exemplary embodiment of the disclosed subject matter.

In exemplary embodiments, the disclosed subject matter provides methods for the oxidative dehydrogenation of butene to produce butadiene. For the purpose of illustration and not limitation, FIG. 1 is a schematic representation of a method according to a non-limiting embodiment of the disclosed subject matter.

In certain embodiments, the method 100 includes providing a feed stream including oxygen and butene in a molar ratio of oxygen to butene ($O_2/C_4H_6$) from about 0.9 to about 1.5 101. For example, the feed stream can be provided to a reactor. As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In certain embodiments, the molar ratio of oxygen to butene ($O_2/C_4H_6$) in the feed stream can be from about 0.9 to about 1.5, from about 0.9 to about 1.3, or from about 0.9 to about 1.1. In particular embodiments, the molar ratio of oxygen to butene ($O_2/C_4H_6$) in the feed stream is about 1.

In certain embodiments, the feed stream can be provided at a specific flow rate. For example, the flow rate of the feed stream can be from about 30 standard cubic centimeters per minute (sccm) to about 800 sccm, from about 150 sccm to about 650 sccm, or from about 250 sccm to about 550 sccm. In certain embodiments, the feed stream can be provided at atmospheric pressure. In other certain embodiments, the feed stream can have a pressure from about atmospheric pressure to about 1 bar, or from about 0.5 bar to about 1 bar.

In certain embodiments, the flow rate of oxygen in the feed stream can be from about 5 sccm to about 60 sccm, from about 10 sccm to about 50 sccm, from about 15 sccm to about 45 sccm, or from about 20 sccm to about 40 sccm. For example, in certain embodiments, the flow rate of oxygen in the feed stream can be about 30.7 sccm. The flow rate of butene in the feed stream can be from about 5 sccm to about 60 sccm, from about 10 sccm to about 50 sccm, from about 15 sccm to about 45 sccm, or from about 20 sccm to about 40 sccm. For example, in certain embodiments, the flow rate of butene in the feed stream can be about 30.7 sccm.

In certain embodiments, the feed stream can further include a diluent. For example, the diluent can be an inert material, e.g., methane, nitrogen, helium, and/or argon. In certain embodiments, the diluent can be methane. In other certain embodiments, the diluent can be a mixture of methane and nitrogen. The flow rate of diluent in the feed stream can be from about 5 sccm to about 60 sccm, from about 10 sccm to about 50 sccm, from about 15 sccm to about 40 sccm, or from about 20 sccm to about 35 sccm. For example, in certain embodiments, the flow rate of diluent in the feed stream can be about 30.7 sccm.

In particular embodiments, the diluent can be methane and the methane can have a flow rate from about 5 sccm to about 60 sccm, from about 10 sccm to about 50 sccm, from about 15 sccm to about 40 sccm, or from about 20 sccm to about 35 sccm. In certain embodiments, the methane can have a flow rate of about 30.7 sccm. In particular embodiments, the diluent can further include nitrogen. The nitrogen can have a flow rate from about 5 sccm to about 60 sccm, or from about 10 sccm to about 50 sccm. In certain embodiments, the nitrogen can have a flow rate of about 10 sccm. In other certain embodiments, the nitrogen can have a flow rate of about 50 sccm.

The method 100 can further include introducing the feed stream to a catalyst in the presence of steam 102. By way of example, and not limitation, the steam can be present in the feed stream, e.g., by mixing the steam with the feed stream prior to introducing the feed stream to the catalyst. For example, the method can include adding steam to the feed stream and vaporizing the feed stream upstream from a reactor.

The presence of steam can reduce the formation of carbonaceous (coke) deposits in the reactor and on the catalyst. Additionally, the presence of steam can decrease the partial pressure of butene and thereby increase butadiene selectivity by favoring the oxidative dehydrogenation reaction. For these and other reasons, the molar ratio of steam to butene can influence catalyst stability and/or butadiene selectivity and/or yield. In certain embodiments, the molar ratio of steam to butene ($H_2O/C_4H_8$) can be from about 10 to about 20, or from about 11 to about 13. In particular embodiments, the molar ratio of steam to butene ($H_2O/C_4H_8$) can be about 12. The flow rate of steam, e.g., in the feed stream, can be from about 150 sccm to about 500 sccm, from about 250 sccm to about 450 sccm, or from about 300 sccm to about 400 sccm. In particular embodiments, the flow rate of steam can be about 365 sccm.

The catalyst for use in the presently disclosed subject matter can be any catalyst type suitable for the oxidative dehydrogenation of butene to form butadiene. For example, in certain embodiments, the catalyst is a zinc-ferrite catalyst. The catalyst can include zinc (Zn) and iron (Fe), and can further include other components, such as cobalt (Co), Magnesium (Mg), Calcium (Ca), Chlorine (Cl) and/or Oxygen (O). In certain embodiments, the catalyst can include silver (Ag), aluminum (Al), cerium (Ce), cesium (Cs), copper (Cu), potassium (K), Lanthanum (La), lithium (Li), manganese (Mn), molybdenum (Mo), sodium (Na), nickel (Ni), phosphorus (P), palladium (Pd), platinum (Pt), ruthenium (Ru), silicon (Si), vanadium (V), tungsten (W), and/or yttrium (Y).

In certain embodiments, the catalyst can have the following formula:

$$FeZn_aCo_bMg_cCa_dCl_eM_fO_x \quad \text{(Formula 1)}$$

With reference to Formula 1, M can include one or more of Ag, Al, Ce, Cs, Cu, K, La, Li, Mn, Mo, Na, Ni, P, Pd, Pt, Ru, Si, V, W, and Y. With further reference to Formula 1, subscripts a, b, c, d, e, f, and x correspond to the molar ratio of each respective component relative to 1 mol of Fe. In certain embodiments, subscripts a, b, c, d, e, f, and/or x can be equal to zero, indicating that one or more components is not present in the catalyst.

In certain embodiments, the method can include preparing the zinc-ferrite catalyst. For example, the zinc-ferrite catalyst can be prepared from a Zn precursor and a Fe precursor. Additionally, the zinc-ferrite catalyst can be prepared from a Co precursor, a Mg precursor, a Ca precursor, and/or another precursor, such as Ag, Al, Ce, Cs, Cu, K, La, Li, Mn, Mo, Na, Ni, P, Pd, Pt, Ru, Si, V, W, and/or Y. By way of example, and not limitation, suitable precursors can include oxide precursors, nitrate precursors, carbonate precursors, halide precursors, and/or combinations thereof. For example, the catalyst can be prepared by mixing the one or more precursors with a solvent, e.g., in water, and subsequently precipitating agglomerated particles to form the catalyst. Non-limiting examples of methods that can be used to prepare the catalysts of the disclosed subject matter are provided in U.S. Patent Publication No. 2013/0217568, which is hereby incorporated by reference.

In certain embodiments, the values of subscripts a, b, c, d, e, f, and/or x can depend on the relative amounts of precursors present during catalyst preparation. For example, the molar ratio of Zn in the Zn precursor ("initial Zn") to Fe in the Fe precursor ("initial Fe") can be less than or equal to about 0.35. In certain embodiments, greater than about 88% of initial Zn is recovered in the catalyst.

In certain embodiments, and with reference to Formula 1, subscript a can range from about 0.07 to about 0.7. Subscript b can range from about 0.01 to about 0.20. Subscript c can be less than or equal to about 0.40. Subscript d can be less than or equal to about 0.40. Subscript e can be less than or equal to about 0.10. Subscript f can be less than or equal to about 0.20. Subscript x can depend on several factors, for example the relative amounts and valence of the other components in Formula 1.

The method 100 can further include reacting the butene in the feed stream to generate a product stream 103. The product stream can include butadiene and water. In certain embodiments, butene ($C_4H_8$) can undergo oxidative dehydrogenation to form butadiene ($C_4H_6$) and water ($H_2O$). The oxidative dehydrogenation of butene can be represented by Formula 2:

$$C_4H_8 + \tfrac{1}{2}O_2 \rightarrow C_4H_6 + H_2O \qquad \text{(Formula 2)}$$

The oxidative dehydrogenation can take place in a reactor. The reactor for use in the presently disclosed method can be any reactor type suitable for the oxidative dehydrogenation of butene. By way of example, and not limitation, such reactors include fixed bed reactors, such as tubular fixed bed reactors or multi-tubular fixed bed reactors, and fluidized bed reactors. The reactors can be operated adiabatically, non-adiabatically, or isothermally.

In certain embodiments, the reactor can be operated isothermally and/or non-adiabatically. For example, the reactor can be maintained at a temperature from about 330° C. to about 370° C. In certain embodiments, the space velocity of the butene can be from about 100 $h^{-1}$ to about 1100 $h^{-1}$, from about 300 $h^{-1}$ to about 900 $h^{-1}$, or from about 400 $h^{-1}$ to about 800 $h^{-1}$. In particular embodiments, the space velocity of the butene can be about 400 $h^{-1}$. In certain embodiments, the total space velocity of the reaction can be from about 1000 $h^{-1}$ to about 11000 $h^{-1}$, or from about 3000 $h^{-1}$ to about 9000 $h^{-1}$, or from about 4000 $h^{-1}$ to about 8000 $h^{-1}$. In particular embodiments, the total space velocity of the reaction can be about 6000 $h^{-1}$.

The method 100 can further include separating water from the product stream to generate a butadiene stream 104. For example, the method can include separating all or a portion of the water from the product stream. In certain embodiments, greater than about 50 wt-%, greater than about 60 wt-%, greater than about 70 wt-%, greater than about 80 wt-%, or greater than about 90 wt-% of the water can be separated from the product stream to generate the butadiene stream. The butadiene stream can contain greater than about 85 wt-% butadiene.

In certain embodiments, butadiene yield can be greater than about 70 wt-%, greater than about 80 wt-%, greater than about 83 wt-%, or greater than about 85 wt-%. Butadiene selectivity can be greater than about 87%, greater than about 89%, greater than about 91%, or greater than about 92%. In certain embodiments, butene conversion can be from about 90% to about 95% and oxygen conversion can be from about 90% to about 99%.

The methods of the presently disclosed subject matter provide advantages over certain existing technologies. Exemplary advantages include increased butadiene yield and feed stream conversion, lower steam consumption, and efficient reactor operation.

The following example provides methods for the oxidative dehydrogenation of butene to form butadiene in accordance with the disclosed subject matter. However, the following example is merely illustrative of the presently disclosed subject matter and should not be considered as a limitation in any way.

Example

In this Example, 6.4 g of a catalyst according to the disclosed subject matter was diluted with quart chips to form a 10 cubic centimeter catalyst bed. The catalyst bed was loaded within a tubular reactor having a ½ inch diameter (OD). Typical reaction conditions are provided in Table 1.

TABLE 1

| | |
|---|---|
| Butene ($C_4H_8$) flow rate | 15-45 sccm |
| Oxygen ($O_2$) flow rate | 15-45 sccm |
| Steam ($H_2O$) flow rate | 250-400 sccm |
| Diluent flow rate | 15-40 sccm |
| $O_2/C_4H_8$ (molar ratio) | 0.5-1.5 |
| $H_2O/C_4H_8$ (molar ratio) | 10-20 |
| Butene space velocity | 400-800 $h^{-1}$ |
| Temperature | 330-370° C. |
| Pressure | atmospheric (0 bar)-1 bar |
| Catalyst bed length | 5-7 inches |
| Vaporizer temperature | 310° C. |
| Catalyst bed temperature rise | 5-30° C. |

Figure 2:
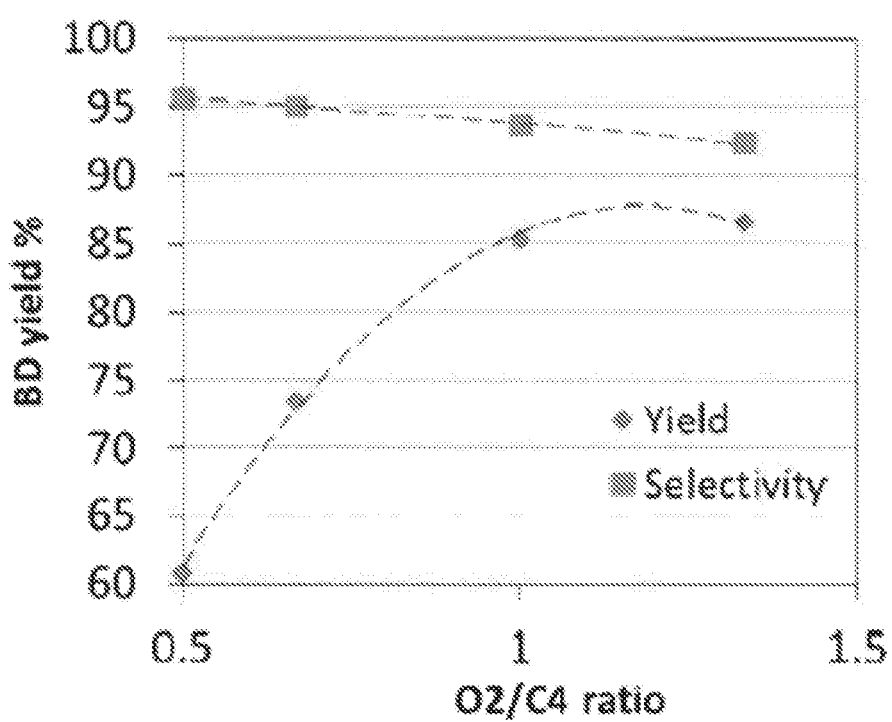
FIG. 2 depicts butadiene selectivity and yield according to certain exemplary embodiments of the disclosed subject matter.
Figure 3:
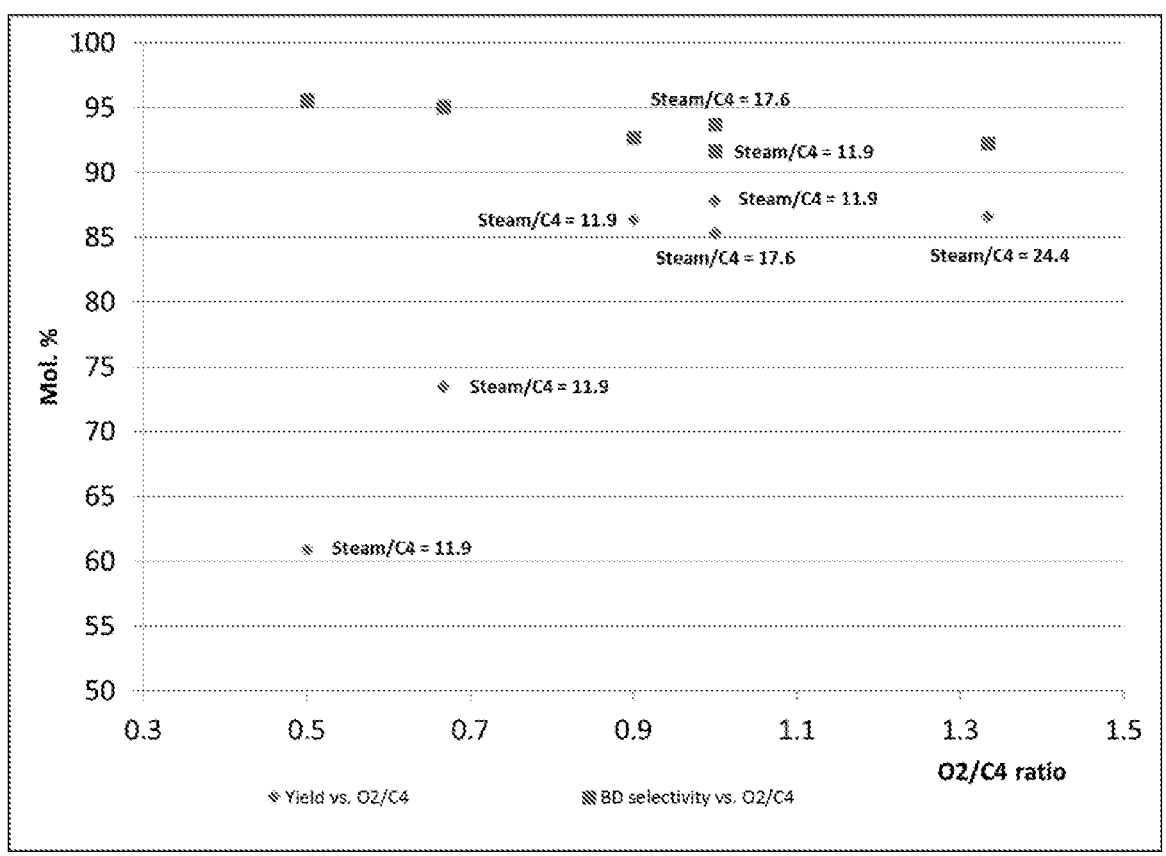
FIG. 3 depicts butadiene selectivity and yield according to certain exemplary embodiments of the disclosed subject matter.

Under these reaction conditions, butene conversion was from 90% to 95% and oxygen conversion was from 90% to 99%. Additionally, FIGS. 2 and 3 show butadiene selectivity and yield over various molar ratios of oxygen to butene ($O_2/C_4H_8$) and steam to butene ($H_2O/C_4H_8$). As shown in FIGS. 2 and 3, butadiene selectivity was greater than about 92%. At molar ratios of oxygen to butene ($O_2/C_4H_8$) from about 0.9 to about 1.5, butadiene yield was greater than about 85 wt-%.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for producing butadiene from a feed stream including oxygen and butene, wherein the molar ratio of oxygen to butene ($O_2/C_4F_{18}$) is 1.5, the method comprising the steps of:
   (a) introducing the feed stream to a catalyst in the presence of steam, wherein the molar ratio of steam to butene ($H_2O/C_4F_{18}$) is 20;
   (b) oxidatively dehydrogenating the butene to generate a product stream therefrom comprising butadiene and water; and
   (c) separating at least a portion of the water from the product stream to generate a butadiene stream comprising 85 wt-% butadiene,
   wherein the reacting is performed under isothermal conditions.

2. The method of claim 1, wherein the feed stream further comprises a diluent.

3. The method of claim 2, wherein the diluent comprises helium.

4. The method of claim 1, wherein the catalyst is a zinc-ferrite catalyst.

5. The method of claim 4, wherein the zinc-ferrite catalyst has a formula $FeZn_aCo_bMg_cCa_dCl_eM_fO_x$, wherein a, b, c, d, e, f, and x correspond to a molar ratio relative to 1 mol of Fe, and wherein:
- a ranges from about 0.07 to about 0.7;
- b ranges from about 0.01 to about 0.20;
- c is less than or equal to about 0.40;
- d is less than or equal to about 0.40;
- e is less than or equal to about 0.10; and
- f is 0.20.

6. The method of claim 5, further comprising preparing the zinc-ferrite catalyst from a Zn precursor, a Fe precursor, a Co precursor, optionally a Mg precursor, optionally a Ca precursor, and optionally a M precursor, wherein the Zn precursor comprises initial Zn and the Fe precursor comprises initial Fe, and the molar ratio of initial Zn to initial Fe is less than or equal to about 0.35.

7. The method of claim 6, wherein the preparing the zinc-ferrite catalyst further comprises preparing the zinc-ferrite catalyst from a Ca precursor and/or a M precursor.

8. The method of claim 5, wherein M is selected from the group consisting of Co and Mg, and combinations thereof.

9. The method of claim 1, further comprising mixing the steam with the feed stream prior to the introducing.

10. The method of claim 1, wherein the reacting is performed at a temperature from about 330° C. to about 370° C.

11. The method of claim 1, wherein 95% of the butene in the feed stream is converted.

12. The method of claim 1, wherein from about 90% to about 95% of the butene in the feed stream is converted.

13. The method of claim 1, wherein from about 90% to about 99% of the oxygen in the feed stream is converted.

14. The method of claim 2, wherein from about 90% to about 95% of the butene in the feed stream is converted.

15. A method for producing butadiene from a feed stream including oxygen and butene, wherein the molar ratio of oxygen to butene ($O_2/C_4H_8$) is from about 0.9 to about 1.5, the method comprising the steps of:
(a) introducing the feed stream to a catalyst in the presence of steam;
(b) oxidatively dehydrogenating the butene to generate a product stream therefrom comprising butadiene and water; and
(c) separating at least a portion of the water from the product stream to generate a butadiene stream comprising greater than about 85 wt-% butadiene, wherein the molar ratio of steam to butene ($H_2O/C_4F_{18}$) is 13.

16. The method of claim 15, further comprising mixing the steam with the feed stream prior to the introducing.

17. The method of claim 15, wherein the butadiene stream comprises greater than about 92 wt-% butadiene.

18. The method of claim 15, wherein from about 90% to about 95% of the butene in the feed stream is converted.

19. A method for producing butadiene from a feed stream including oxygen and butene, wherein the molar ratio of oxygen to butene ($O_2/C_4H_8$) is from about 0.9 to about 1.5, the method comprising the steps of:
(a) introducing the feed stream to a catalyst in the presence of steam, wherein the molar ratio of steam to butene ($H_2O/C_4H_8$) is from about 10 to about 20;
(b) oxidatively dehydrogenating the butene to generate a product stream therefrom comprising butadiene and water; and
(c) separating at least a portion of the water from the product stream to generate a butadiene stream comprising 85 wt-% butadiene, wherein the reacting is performed under isothermal conditions and non-adiabatic conditions, and wherein the reacting is performed at a temperature from about 330° C. to about 370° C.

20. The method of claim 19, wherein the molar ratio of steam to butene ($H_2O/C_4H_8$) is about 11.

* * * * *

UNITED STATES PATENT AND TRADEMARK OFFICE
CERTIFICATE OF CORRECTION

PATENT NO. : 10,532,963 B2  
APPLICATION NO. : 16/062541  
DATED : January 14, 2020  
INVENTOR(S) : Xin Li et al.

Page 1 of 1

It is certified that error appears in the above-identified patent and that said Letters Patent is hereby corrected as shown below:

In the Claims

Column 7, Claim 5, Line 4, delete "$FeZn_aCo_bMg_cCa_dCl_eM_tO_x$" and replace with --$FeZn_aCo_bMg_cCa_dCl_eM_fO_x$--.

Column 8, Claim 15, Line 13, delete "$H_2O/C_4F_{18}$" and replace with --$H_2O/C_4H_8$--.

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*